(12) United States Patent
Albrecht et al.

(10) Patent No.: US 10,957,046 B2
(45) Date of Patent: Mar. 23, 2021

(54) AUTOMATIC QUALITY CHECKS FOR RADIOTHERAPY CONTOURING

(71) Applicant: Varian Medical Systems International AG, Cham (CH)

(72) Inventors: Thomas Albrecht, Basel (CH); Peter Hess, Urdorf (CH); Nawal Houhou, Nussbaumen (CH)

(73) Assignee: VARIAN MEDICAL SYSTEMS INTERNATIONAL AG, Steinhausen (CH)

( * ) Notice: Subject to any disclaimer, the term of this patent is extended or adjusted under 35 U.S.C. 154(b) by 237 days.

(21) Appl. No.: 16/252,848

(22) Filed: Jan. 21, 2019

(65) Prior Publication Data

US 2019/0172210 A1 Jun. 6, 2019

Related U.S. Application Data

(63) Continuation of application No. 15/273,454, filed on Sep. 22, 2016, now Pat. No. 10,290,093.

(Continued)

(51) Int. Cl.
| | |
|---|---|
| *G06K 9/00* | (2006.01) |
| *G06T 7/143* | (2017.01) |
| *G06T 7/00* | (2017.01) |
| *G06T 7/12* | (2017.01) |
| *G06T 7/50* | (2017.01) |
| *G06T 7/13* | (2017.01) |
| *G16H 30/20* | (2018.01) |
| *G06F 16/54* | (2019.01) |
| *G06N 7/00* | (2006.01) |

(52) U.S. Cl.
CPC .............. *G06T 7/143* (2017.01); *G06F 16/54* (2019.01); *G06N 7/005* (2013.01); *G06T 7/001* (2013.01); *G06T 7/0002* (2013.01); *G06T 7/0012* (2013.01); *G06T 7/12* (2017.01); *G06T 7/13* (2017.01); *G06T 7/50* (2017.01); *G16H 30/20* (2018.01); *G06K 2209/05* (2013.01); *G06T 2207/10081* (2013.01); *G06T 2207/10116* (2013.01); *G06T 2207/20076* (2013.01); *G06T 2207/20212* (2013.01); *G06T 2207/30008* (2013.01); *G06T 2207/30048* (2013.01); *G06T 2207/30096* (2013.01); *G06T 2207/30168* (2013.01); *G06T 2207/30242* (2013.01)

(58) Field of Classification Search
None
See application file for complete search history.

(56) References Cited

U.S. PATENT DOCUMENTS

| | | | |
|---|---|---|---|
| 2005/0180621 A1* | 8/2005 | Raman | A61B 6/504 |
| | | | 382/128 |
| 2009/0297014 A1 | 12/2009 | Nelms et al. | |

(Continued)

OTHER PUBLICATIONS

Kim et al., "Process monitoring based on probabilistic PCA," Chemometrics and Intelligent Laboratory Systems, vol. 67, 2003, pp. 109-123.

(Continued)

*Primary Examiner* — Atiba O Fitzpatrick
(74) *Attorney, Agent, or Firm* — SGPatents PLLC

(57) ABSTRACT

Systems, devices, methods, and computer processing products for automatically checking for errors in segmentation (contouring) using heuristic and/or statistical evaluation methods.

23 Claims, 7 Drawing Sheets

Related U.S. Application Data

(60) Provisional application No. 62/221,921, filed on Sep. 22, 2015.

(56) References Cited

U.S. PATENT DOCUMENTS

| | | |
|---|---|---|
| 2013/0259382 A1 | 10/2013 | Math |
| 2014/0341449 A1 | 11/2014 | Tizhoosh et al. |
| 2018/0158201 A1* | 6/2018 | Thompson ............... G06T 7/11 |

OTHER PUBLICATIONS

Heimann et al., "Statistical shape models for 3D medical image segmentation: a review," Medical Image Analysis, vol. 13, 2009, pp. 543-563.

Chen et al., "Automated contouring error detection based on supervised geometric attribute distribution models for radiation therapy: a general strategy," Med. Phys., vol. 42 (2), Feb. 2015, pp. 1048-1059.

Kong et al., "Consideration of dose limits for organs at risk of thoracic radiotherapy: atlas for lung, proximal bronchial tree, esophagus, spinal cord, ribs, and brachial plexus," Int. J Radiat. Oncol. Biol. Phys., vol. 81 (5), Dec. 2011, pp. 1442-1457. doi:10.1016/j.ijrobp.2010.07.1977.

Filippi et al., "Innovative technologies in thoracic radiation therapy for lung cancer," TLCR, vol. 1 (4), Dec. 2012. doi:10.3978/j.issn.2218-6751.2012.10.06.

Shirai et al., "Use of FDG-PET in radiation treatment planning for thoracic cancer," International Journal of Molecular Imaging, vol. 2012 (2012), Article ID 609545, 9 pages.

Liu et al., "Research on contour correction in medical CT image segmentation," Journal of Computers, vol. 7 (3), Mar. 2012, pp. 762-767.

Vellker et al., "Creation of RTOG compliant patient CT-atlases for automated atlas based contouring of local regional breast and high-risk prostate cancers," Radiation Oncology, vol. 8 (188), 2013, 8 pages.

Burger et al., "Regions in binary images," Principles of Digital Image Processing, 2009. doi:10.1007/987-1-84800-195-4_2.

Maire, "Contour detection and image segmentation," University of California, Berkley, 2009.

Zhou et al., "Interactive contour delineation and refinement in treatment planning of image-guided radiation therapy," Journal of Applied Clinical Medical Physics, vol. 15 (1), 2014.

"Processing Binary Images," 2002 by CRC Press LLC.

Ramkumar et al., "Comparison of heuristic evaluation and think aloud methods: a study in radiotherapy contouring software," International Symposium on Human Factors and Ergonomics in Health Care: Advancing the Cause, 2014, pp. 230-237.

"Appendix E: radiotherapy treatment planning and quality assurance protocol," TREC, Sep. 2011, 20 pages.

Michalski, "Medulloblastoma target volumes and organ at risk atlas," ACNS0331.

"The role of PET/CT in radiation treatment planning for cancer patient treatment," IAEA-TECDOC-1603, Oct. 2008.

Kardell, "Automatic segmentation of tissues in CT images of the pelvic region," Linkoping University, Department of Biomedical Engineering, Nov. 2014, LiTH-IMT/BIT30-A-EX—14/521—SE.

* cited by examiner

Image slice with manually drawn contours of the different regions of interest (ROIs)

Image slice

Example Data · Statistical Model

Given Segmentation · Best Shape Model Fit

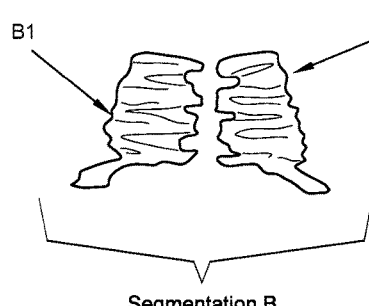
Fig. 11A — Segmentation B
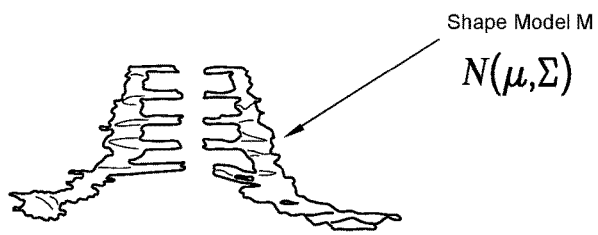
Fig. 11B — Shape Model M $N(\mu,\Sigma)$
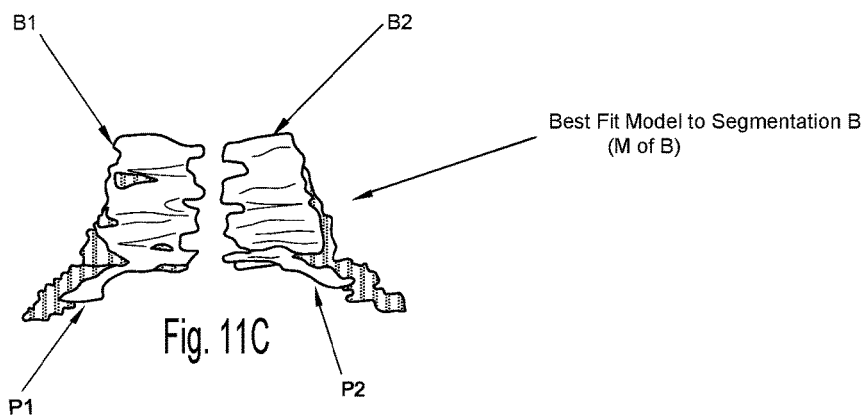
Fig. 11C — Best Fit Model to Segmentation B (M of B)
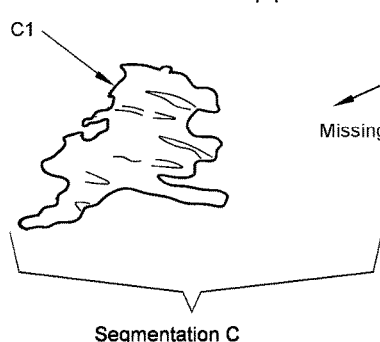
Fig. 12A — Segmentation C
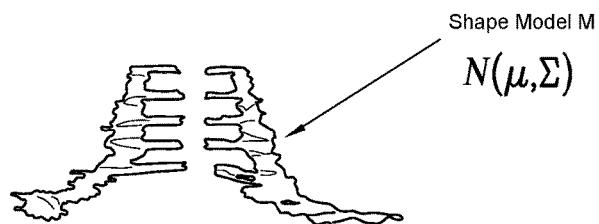
Fig. 12B — Shape Model M $N(\mu,\Sigma)$
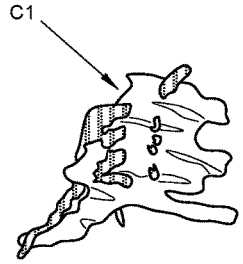
Fig. 12C — Best Fit Model to Segmentation C (M of C)

AUTOMATIC QUALITY CHECKS FOR RADIOTHERAPY CONTOURING

FIELD

The present disclosure relates generally to radiation therapy, and more particularly, to systems devices, and methods for automated verification of contours.

BACKGROUND

Radiosurgery and radiotherapy play an important role in the treatment of cancers. In general, radiosurgery and radiotherapy treatments consist of several phases. First, a precise three-dimensional (3D) map of the anatomical structures in the area of interest (head, body, etc.) is constructed to determine the exact coordinates of the contour within the anatomical structure, namely, to locate the tumor or abnormality within the body and define its exact shape and size. Second, a motion path for the radiation beam is computed to deliver a dose distribution that the surgeon finds acceptable, taking into account a variety of medical constraints. During this phase, a team of specialists develop a treatment plan using special computer software to optimally irradiate the tumor and minimize dose to the surrounding normal tissue by designing beams of radiation to converge on the contour area from different angles and planes. The third phase is where the radiation treatment plan is executed. During this phase, the radiation dose is delivered to the patient according to the prescribed treatment plan using radiation treatment techniques, such as intensity-modulated radiation therapy (IMRT) and volumetric modulated arc therapy (VMAT), for example.

These techniques are typically used with a radiotherapy system, such as a linear accelerator (linac), equipped with a multileaf collimator (MLC) to treat pathological anatomies (tumors, lesions, vascular malformations, nerve disorders, etc.) by delivering prescribed doses of radiation (X-rays, gamma rays, electrons, protons, particles, and/or ions) to the pathological anatomy while minimizing radiation exposure to the surrounding tissue and critical anatomical structures.

Accurate delineation, also known as segmentation or contouring, of targets, tumors, organs at risk (OAR), for example, is essential in treatment planning. Accurately delineating the targets, tumors, and organs at risk, is an important factor in preventing geographic misses in radiotherapy planning. For example, an underestimation of tumor extension will result in tumor recurrence. In contrast, overestimation of the tumor extension may increase unnecessary side effects.

Accurate delineation of contours requires the identification of anatomic borders of the contours such as tumors and OARs based on accurate diagnosis. Currently, delineation (contouring) can be done manually, semiautomatically, or automatically. While such "contouring" is typically reviewed by trained staff, a risk remains that errors are introduced and passed on to the next steps in the radiotherapy planning.

BRIEF SUMMARY

The embodiments disclosed herewith provide systems, devices, and methods for automatic detection of contouring errors to increase the efficiency of the radiotherapy planning process and also improve patient safety. The embodiments disclosed herewith also provide a set of contour evaluation methods that can be automatically performed by a computer processing device in order to rule out a number of segmentation errors.

In an embodiment, a method is provided for automatically detecting segmentation (contouring) errors by generating one or more segments (contours), and automatically evaluating the one or more segments (contours) using a heuristic evaluation method and/or a statistical evaluation method. The evaluation of the one or more contours by a heuristic evaluation method comprises setting a set of heuristic rules, and determining whether at least one of the heuristic rules has been violated. If at least one of the heuristic rules has been violated, a determination can be made that there is an error in the contour. The determination of whether a heuristic rule has been violated can be done by evaluating the one or more segments using Boolean operations and pixel/voxel counting, and/or by evaluating the one or more segments (contours) using a 3-dimensional (3D) connectivity labeling process.

The Boolean operation method can include generating binary images for the segments, combining the binary images using at least one of a plurality of Boolean operators to generate a resulting binary image, and determining whether the resulting binary image satisfies the heuristic rule by counting pixels/voxels in the resulting binary image. If the number of pixels/voxels is judged to not be within a predetermined range, it is concluded that the heuristic rule has been violated, which would indicate that an error is present in the one or more contours.

The evaluation of the one or more contours by the statistical evaluation method includes evaluating a shape of the contour and determining whether the shape of the contour is within a predetermined range of known shapes for the contour. The evaluation method comprises generating a shape model based on a probabilistic distribution of shape variations found in the range of known shapes for the contour, and performing a statistical test to check if the shape of the contour is within the predetermined range. The probabilistic distribution can include a multivariate normal distribution $\mathcal{N}(\mu,\Sigma)$.

The performing of the statistical check can also comprise evaluating how well the contour shape fits within the multivariate normal distribution using a probabilistic principal component analysis (PPCA). If the shape of the contour does not fit within the multivariate normal distribution within a predetermined probability, it is determined that a segmentation error is present.

Regardless of the evaluation method used, once it is determined that a contouring error is present, a warning signal alerting that a segmentation error is present can be displayed on a display device of the processing system, or the treatment planning system, or any other display device connected to an output of the segmentation error determination device. A segmentation (contouring) report including the results of the segmentation (contouring) evaluation can also be displayed or printed.

In other embodiments, the determination whether at least one of the heuristic rules has been violated can also include evaluating the one or more segments (contours) using a three-dimensional (3D) connectivity labeling process.

The evaluation of the segments (contours) can be done in real time.

Systems for automatically performing the checking for errors in segmentation (contouring) are also disclosed. In one embodiment, the system comprises an imaging device configured to generate one or more image slices of a contour, and to mark segments (contours) of one or more contour on the image slices, and a computer processing device configured to automatically evaluate the segments (contours) using a heuristic and/or a statistical evaluation method.

The computer processing device can comprise a database including a set of heuristic rules, wherein the automatic evaluation includes checking whether one or more of the segments (contours) are violating at least one of the heuristic rules. The computer processing device can be further configured to generate binary images for the segments (contours) and to combine the binary images using one or more Boolean operators. The computer processing device can be further configured to generate a binary image which is a result of the combining of the binary images using the one or more Boolean operators, and evaluate whether the resulting binary image complies with a heuristic rule using a pixel/voxel counting process.

The system can further comprise a display device to display an error signal if it is determined by the computer processing device that the resulting binary image fails to comply with a heuristic rule. The system can further display an error message if it is determined by the computer processing device that the contour (i.e., organ, for example) shape is not within a range of known contour (organ) shapes.

In embodiments, the computer processing device is further configured to implement a statistical shape model to determine if the shape of the contour fits within a predetermined range of shapes for this contour.

In embodiments, a non-transitory computer readable medium containing program instructions for automatically evaluating segments (contours) is also disclosed, wherein execution of the program instructions by a computer processing device causes the computer processing device to carry out the evaluation steps recited above, and disclosed herein.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features.

FIG. 11A illustrates an example of a segmentation to which a shape model is applied, according to embodiments of the present invention.

FIG. 11B illustrates an example of a shape model to be applied to the segmentation of FIG. 11A.

FIG. 11C illustrates the best fit model applied to the segmentation of FIG. 11A using the shape model of FIG. 11B.

FIG. 12A illustrates an example of a segmentation to which a shape model is applied, according to embodiments of the present invention.

FIG. 12B illustrates an example of a shape model to be applied to the segmentation of FIG. 12A.

FIG. 12C illustrates the best fit model applied to the segmentation of FIG. 12A using the shape model of FIG. 12B.

DETAILED DESCRIPTION

The primary aim of radiotherapy planning is to maximize radiation dose to a patient's tumor while sparing normal tissues and organs at risk. To achieve this, the boundary of the tumor needs to be accurately identified. Tumor delineation typically includes delineation (contouring) of gross, clinical, and planning target volumes for a structure of interest. The gross tumor volume (GTV) is the volume of all gross sites of disease (primary, nodal, and extramural vascular invasion). The clinical target volume (CTV) encompasses areas of microscopic spread beyond the defined GTV. The clinical target volume (CTV) includes two distinct volumes, CTVA and CTVB, with CTVA including GTV+~1 cm, for example, to define the surrounding safety margin of potential subclinical involvement (superior, inferior, anterior, and posterior), and CTVB including the organs at risk of involvement. The final clinical target volume (CTVF) is a product of combining CTVA and CTVB. The planning target volume (PTV) is defined as CTVF+~1 cm, (superiorly, inferiorly, anteriorly, and posteriorly), for example, to ensure coverage of the CTV taking into account the systematic and random setup errors, changes over time in the patient geometry and internal organ movement that may occur when delivering a course of radiation. Any other combinations of target volumes, such as, the combination of gross tumor volume GTV, the clinical target volume CTV, and the planning target volume PTV, for example, can also be used for tumor delineation during the planning. Besides target volumes, any other structures of interest, such as different organs at risk, for example, can also be delineated during the planning.

Figure 5:
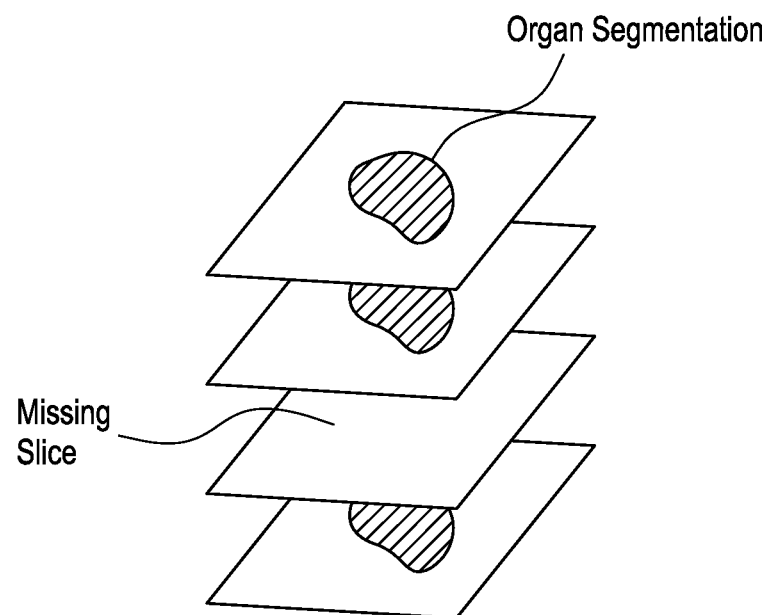
FIG. 5 illustrates an example of a segmentation of an organ at risk with a missing slice.
Figure 6:
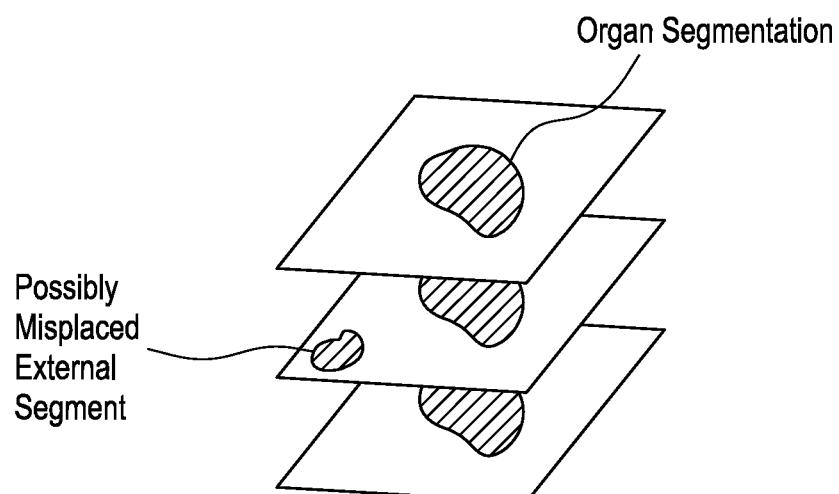
FIG. 6 illustrates an example of a segmentation of an organ at risk with an unintentionally placed small contour outside the organ.

Tumor delineation is performed by physicians, either manually or using semi-automatic/automatic software based on images of the patient obtained using an imaging method, such as, but not limited to, computed tomography (CT), positron emission tomography (PET), and/or magnetic resonance imaging (MRI), for example. Delineating the structures of interest, such as the radiation target volumes, as well as the organs at risk (i.e., organs that should be spared from radiation), involves marking or "segmenting" the structures of interest on each image slice obtained using the CT, PET and/or MRI images. Then, the contours are visually evaluated by trained medical staff. Although the contours are reviewed by trained staff, errors due to interobserver variation may be introduced and passed on to the next steps in radiotherapy planning. If undetected, these errors will propagate throughout the planning phase, and it will ultimately affect the patient. Typical examples of such errors are missing slices in the segmentation of an organ at risk and unintentionally placed small contours outside the organ. FIG. 5 illustrates an example of a segmentation of an organ at risk with a missing slice, and FIG. 6 illustrates an example of a segmentation of an organ at risk with an unintentionally placed small contour outside the organ. These errors will propagate through later stages of radiotherapy planning if they remain undetected.

The present embodiments provide systems, devices, and methods to automatically detect contouring errors to increase the efficiency of the radiotherapy planning process and also improve patient safety. The embodiments provide a set of contour evaluation methods that can be automatically performed by a computer processing device in order to rule out a number of segmentation errors.

In operation, prior to the contour evaluation process and prior to the treatment planning phase, a precise three-dimensional (3D) map of the anatomical structures in the area of interest (head, body, etc.) is constructed using any one of a computed tomography (CT), cone-beam CBCT, magnetic resonance imaging (MRI), positron emission tomography (PET), 3D rotational angiography (3DRA), or ultrasound techniques. This determines the exact coordinates of the contour within the anatomical structure, namely, locates the tumor or abnormality within the body and defines its exact shape and size.

Figure 1:
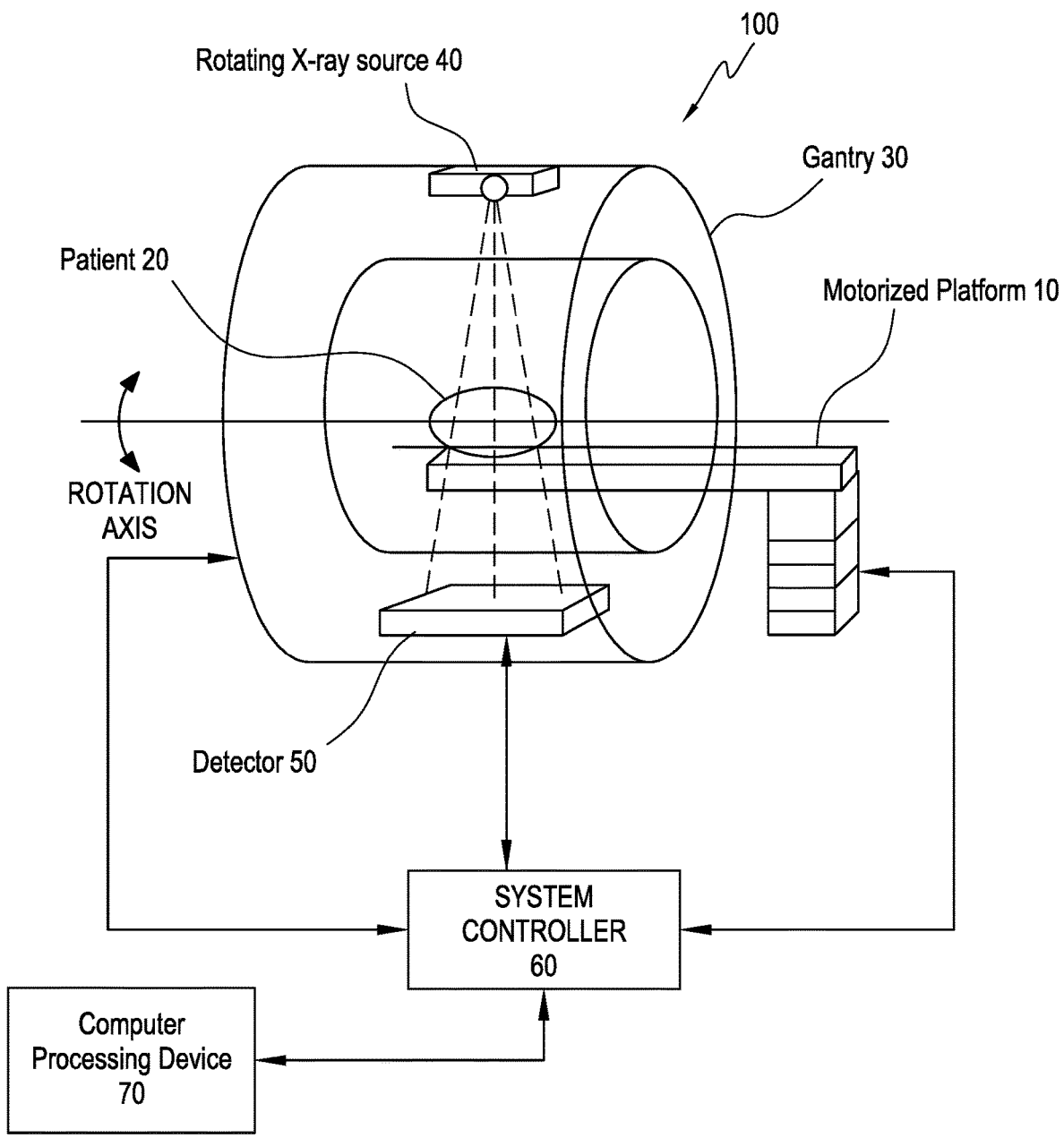
FIG. 1 illustrates a computed tomography (CT) system according to one or more embodiments of the disclosed subject matter.

In an exemplary embodiment, a computed tomography (CT) system 100, as shown in FIG. 1, is used to generate the images for the 3D map. A motorized platform (table) 10 moves the patient 20 through the circular opening of the gantry 30 of the CT imaging system 100. As the patient 20 passes through the CT imaging system, a source of x-rays 40 rotates around the inside of the circular opening. A single rotation can take about 1 second. The x-ray source 40 produces a narrow, fan-shaped beam of x-rays used to irradiate a section of the patient's body. The thickness of the fan beam may be as small as 1 millimeter or as large as 10 millimeters, for example. In examinations there are several phases, each made up of 10 to 50 rotations of the x-ray source 40 around the patient 20 in coordination with the platform 10 moving through the circular opening. The patient 20 may receive an injection of a contrast material to facilitate visualization of vascular structure.

One or more detectors, such as one or more Electronic Portal Imaging Devices (EPIDs) 50, for example, on the exit side of the patient 20 record the x-rays exiting the section of the patient's body being irradiated as an x-ray "snapshot" at one position (angle) of the source of x-rays 40. Many different "snapshots" (angles) are collected during one complete rotation. The data is then sent to a system controller 60 including a computer processing device to reconstruct all of the individual "snapshots" into a cross-sectional image (i.e., image slice) of the structures, such as the internal organs and tissues, for each complete rotation of the source of x-rays 40.

The system controller 60 includes a processor that is integrated into the imaging system, or could be a separate computer processing device 70 that is connected to the imaging device 100. The controller 60 and/or the computer processing device 70 can include a computer with typical hardware, such as a processor, and an operating system for running various software programs and/or communication applications. The computer can include software programs that operate to communicate with the imaging device 100. The software programs are operable to receive data from external software programs and hardware. The controller and/or the computer processing device 70 can also include any suitable input/output devices adapted to be accessed by medical personnel, as well as input/output (I/O) interfaces, storage devices, memory, keyboard, mouse, monitor, printers, scanners, etc. The controller 60 and/or the computer processing device 70 can also be networked with other computers and radiation therapy systems. Both the imaging device 100 as well as the computer processing device 70 can communicate with a network as well as a database and servers. The controller 60 and/or the computer processing device 70 can also be configured to transfer medical image related data between different pieces of medical equipment.

The imaging system 100, the system controller 60 and/or the computer processing device 70 can also include a plurality of modules containing programmed instructions (e.g., as part of the computer processing system and/or the imaging system, or integrated into other components of the imaging system, or as separate modules within the imaging system), which instructions cause the imaging system to allow all image guidance activities, such as, image acquisition, image registration, image interpretation, image evaluation, capture of data needed for image acquisition and evaluation, image transformation, image transfer, contour generation, contour extraction, contour evaluation, image display, contour display, and/or results display, as discussed herein, when executed.

The interface of the controller 60 and/or the computer processing device 70 is configured to allow a user to input data, manipulate input and output data, and make any edits to the data, to the contour, and to the displayed output. The modules can be written in C or C++ programming languages, for example. Computer program code for carrying out operations as described herein may also be written in other programming languages.

The cross-sectional images (i.e., image slices) of the variety of structures, such as the internal organs and tissues, for example, obtained during the imaging of the patient 20 using the CT system 100 can be stored in a storage device of the controller 60, or a storage device of the computer processing device 70, or in an external storage device accessible by the system controller 60 and the computer processing device 70, for further processing. Although the images in the exemplary embodiment have been obtained using a CT system and an x-ray source, any other imaging systems and radiation sources may be used.

Once the image slices are obtained using the CT, PET, MRI, or any other used imaging methods, different segmentation techniques can be applied on the image slices to delineate a variety of structures (e.g., organs, anatomy, tissue, etc.). Such segmentation can be performed manually, semiautomatically or fully automatically. In embodiments, the contours may also be segmented on separately obtained images and transferred to the main planning image.

Figure 2:
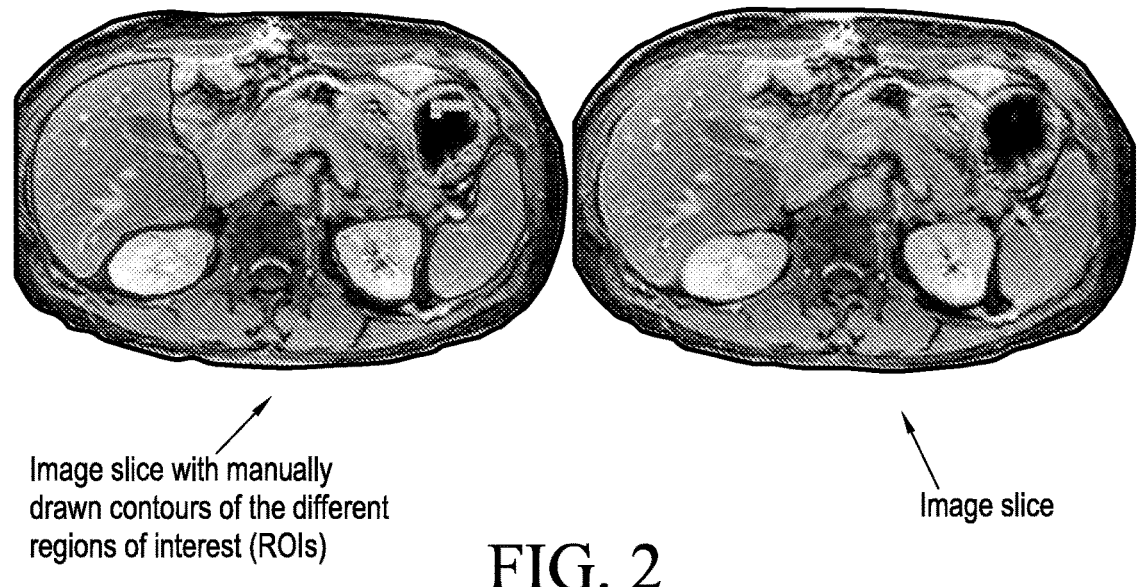
FIG. 2 illustrates manual contouring of an image slice according to one or more embodiments of the disclosed subject matter.

Manual techniques, such as shown in FIG. 2, allow users to outline structures manually or using software, such as, but not limited to, the ANALYZE software package. During manual segmentation, a user manually draws contours around different structures of interest, such as a tumor, organs, organs at risk, a tissue segment, etc. Although manual segmentation may be accurate, it is time-consuming and tedious for users. Also, manual segmentation causes interobserver variation or bias.

Figure 3:
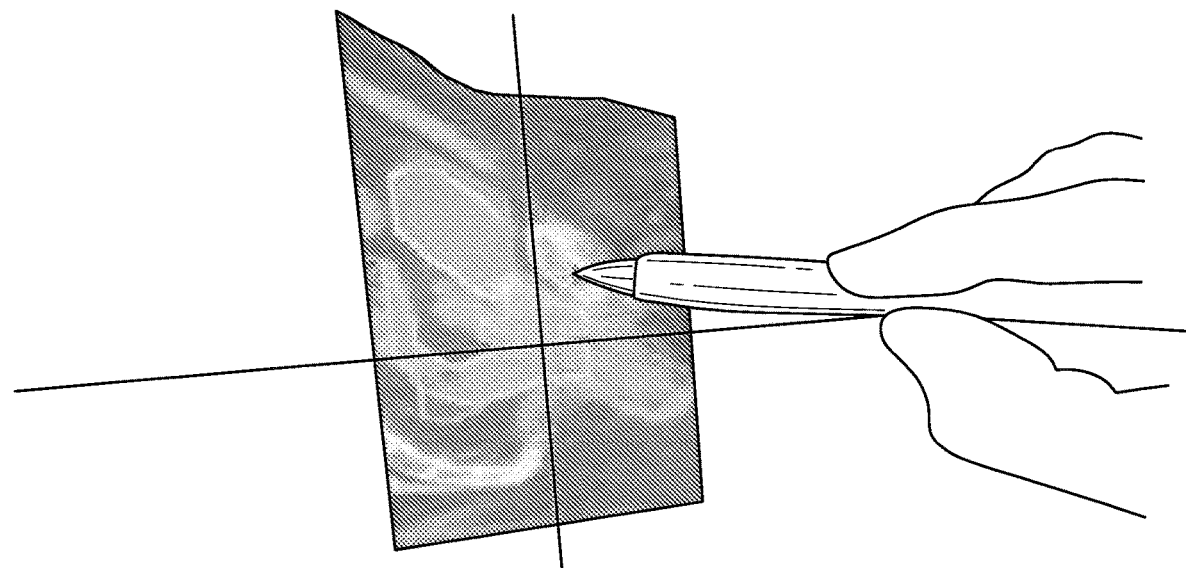
FIG. 3 illustrates a semiautomatic contouring of a CT image slice according to one or more embodiments of the disclosed subject matter.

Semiautomatic techniques, such as shown in FIG. 3, allow the user to have some control or input into the segmentation process, combined with some automatic process using computer algorithms. Semiautomatic approaches based on thresholding, region growing, and deformable models, can be used in numerous applications.

Fully automatic techniques require no user input and often make use of some prior knowledge from the anatomy being segmented to produce the segmentation or delineation. Two examples of these approaches are atlas-based segmentation and statistical shape model segmentation.

There are many available toolkits provided by commercial software for delineation, such as the contour tools provided by iPlan, Eclipse, and Pinnacle, that can be used for contouring. For example, the iPlan RT image (BrainLAB, Feldkirchen, Germany) provides automatic delineation for structures, and fast contouring is achieved with unique, atlas-based automatic organ segmentation. In Eclipse treatment planning system (Varian Medical Systems, Palo Alto, Calif.), SmartAdapt contouring is achieved by automatically deforming and propagating initial contours to match the current anatomy, and editing or fine tuning the changes using a variety of two-dimensional (2D) and three-dimensional (3D) contour edition features. This is a semi-automatic method that combines automatic contouring and manual revision. On Pinnacle (Philips Healthcare, Andover, Mass.) contours are completed using autocontour and autothreshold tools. The model based segmentation (MBS) software of Pinnacle includes an anatomic library of 3D patient organ structure models, which reduces the time spent manually drawing contours. Any of the above described delineation methods, or other applicable delineation methods, can be used to obtain the contours herein.

After the delineation, the image slices containing the contours are stored in a database of the controller 60 and/or the computer processing device 70 for contour evaluation. The image slices may be stored as digital images.

In order to automatically evaluate the contours, a set of evaluation methods are stored in the system controller 60 and/or the computer processing device 70 and/or the external storage device. When executed by the system controller 60 or the computer processing device 70, the set of evaluation methods automatically checks the contours marked on each image slice to rule out a number of segmentation errors. The execution of the set of evaluation methods can be automatically initiated after the segmentation process is finished, or can be initiated by a user at will. The selection of the evaluation methods within the set, as well as the order of execution of the evaluation methods can be done automatically without user input or can be controlled by the user. The selection of the methods and/or the order may depend on different previously determined parameters, including but not limited to, the type of the segmented structure, the type of image obtained, the type of segmentation process used to obtain the contours, etc. The user inputs may be done using a user interface communicating with the computer processing device 70 and/or the system controller 60.

These automatic computerized evaluation methods include, but are not limited to, heuristic evaluation methods and statistical shape model evaluation methods.

Heuristic Evaluation Method

Heuristics are rules of thumb for reasoning, simplification, and educated guess that reduce or limit the search for solutions for a complex problem. Since the problem that the present invention seeks to solve, namely, to determine whether a given segmentation is correct, is a complex one, applying a heuristic evaluation method to solve the problem allows for a simplified way to make a contour error determination.

The proposed heuristic evaluation method includes a set of rules that are quality checks for testing whether the obtained contours adhere to a set of common-sense rules. These rules are predefined checks which are used to identify contouring errors. For example, one of the rules is that the contoured organ must be a single connected structure with no missing slices or accidentally misplaced contours. Another rule checks that different contours of different organs do not overlap each other. Depending on the type of the structure of interest, different rules may be applied. The rule parameters (e.g., thresholds) may also vary. The execution of the one or more rules within the heuristic evaluation method can be automatically initiated after the segmentation process is finished, or can be initiated by a user at will. The selection of the rules and/or combination of rules to be used, and the order of execution of the selected rules can be done automatically using a determination engine to determine which rules are applicable and/or desired based on a previously determined and compiled set of parameters, such as, but not limited to, the type of the segmented structure. The selection of the rules and/or combination of rules to be used, and the order of execution of the selected rules can also be done via user input, where the user selects from the set of rules which ones to be used, and in which order. The selection may depend on different previously determined parameters, including but not limited to, the type of the segmented structure, the type of image obtained, the type of segmentation process used to obtain the contours, etc. The user inputs may be done using a user interface communicating with the computer processing device 70 and/or the system controller 60.

The following heuristic rules can be applied in one or more embodiments disclosed herein. This list is only exemplary, and other heuristic rules may also be applied alone or in combination with any of the listed rules:

1) The structure must be inside the contour of the body;
2) The structure must not overlap with another structure;
3) The structure must not contain any empty slices;
4) The structure must be one single 3D connected contour;
5) Length or volume, or other quickly computed shape features of the structure, must be in a predefined typical range;
6) The left and right paired structures, such as lungs, eyes, kidneys, femurs, etc. for example, are not switched by mistake;
7) The CTV structures are completely covered by at least one PTV structure;
8) The GTV structures are completely covered by at least one CTV structure;
9) The organ at risk is contoured in a sufficient area around the PTV.

Not all rules apply to each organ. For example, there are organs that are not a single connected structure, and therefore some of these rules do not apply. The selection of specific rules that can be applied to each organ and tissue may be based on predefined radiotherapy atlases, such as the radiotherapy atlas for the delineation of organs at risk for a thoracic radiotherapy described in "Consideration of Dose Limits for Organs at Risk of Thoracic Radiotherapy: Atlas for Lung, Proximal Bronchial Tree, Esophagus, Spinal Cord, Ribs, and Brachial Plexus," by Feng-Ming (Spring) Kong et al., in International Journal of Radiation Oncology*Biology*Physics, 2011, for example, which is incorporated herein by reference in its entirety. Any other predefined radiotherapy atlases may be used for the selection of the heuristic check rules to be applied for organs or tissues.

Figure 8:
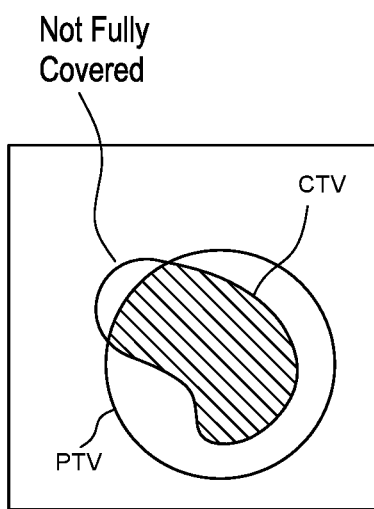
FIG. 8 illustrates an example of a segmentation with a CTV structure that is not fully covered by a PTV structure.

In an exemplary embodiment, a heuristic rule is applied to require that a structure is inside the contour of the body. In another exemplary embodiment, a heuristic rule is applied to require that the structure does not overlap with another structure. In another exemplary embodiment, a heuristic rule is applied to require that the structure does not contain any empty slices (e.g., as illustrated in FIG. 5). In another exemplary embodiment, a heuristic rule is applied to require that the structure is a single 3D-connected contour. In another exemplary embodiment, a heuristic rule is applied to require that quickly computed shape features such as length or volume are in a predefined range. In another exemplary embodiment, a heuristic rule is applied to require that the left and right lung structures are not switched by mistake (i.e., the left lung lies to the left of the right lung). In another exemplary embodiment, a heuristic rule is applied to require that the clinical target volume (CTV) structures (e.g., the tumor plus an additional area for possible disease spread) are completely covered by at least one planning target volume (PTV) structure (e.g., CTV plus an additional area to account for uncertainties in planning/treatment delivery). An example of a segmentation with a CTV structure that is not fully covered by a PTV structure is illustrated in FIG. 8.

In another exemplary embodiment, a heuristic rule is applied to require that gross tumor volume (GTV) structures (e.g., size and position of imaged/seen gross tumors) are completely covered by at least one CTV structure. In another exemplary embodiment, a heuristic rule is applied to require that the organ at risk is contoured in a sufficient area around a PTV.

In exemplary embodiments, all applicable heuristic rules are used. In other embodiments, one or more heuristic rules alone or in combination may be used.

The implementation of one or more heuristic rules is achieved based on pixel and/or voxel (i.e., a region in a slice that corresponds to a pixel in an image) counting and Boolean operations (e.g., intersection and subtraction, etc.) of structures. This can be done as follows:

The segments (contours) on each image slice obtained using one of the variety of imaging applications (CT, PET-CT, MRI, ultrasound) are converted into binary images. In some embodiments conversion is not needed since the contours have already been represented as binary images. This depends on how the 3D segmentation software represents the contours in the first place. Since the segments (contours) represent subsets of the 3D space, often only their surface is considered, namely a 2D surface in 3D space. The 3D segmentation software can choose one or several of the following contour representations.

1.) Polygonal meshes of the surface. This is most common in computer graphics. A polygon mesh is a collection of vertices, edges and faces that defines the shape of an object in 3D computer graphics and solid modeling. The faces usually consist of triangles (triangle mesh), quadrilaterals, or other simple convex polygons, since this simplifies rendering, but may also be composed of more general concave polygons, or polygons with holes. In this representation, the segment (contour) is defined as the 3D space inside the polygon mesh.

2.) Contours stacks. This is generally used in Digital Imaging and Communications in Medicine (DICOM), which is a standard for handling, storing, printing, and transmitting information in medical imaging. It includes a file format definition and a network communications protocol. The communication protocol is an application protocol that uses TCP/IP to communicate between systems. In DICOM, for each slice of the original image (planning CT), a polygonal contour is stored. This contour outlines all pixels on that slice that belong to the structure. The 3D stack of all these pixels defines the segment (contour) in this representation.

3.) Binary images or label maps. These are digital images that have only two possible values for each pixel or voxel, usually black and white. The values need not be binary, however. Values such as 0 and 255 with a smooth transition in between can be used. A signed distance map with value 0 on the surface and negative values inside can also be used. Positive values can also be used. In a label map, more than one segment can be represented in one image. In this representation, the segment (contour) is defined as the set of voxels that have a specific value or value range. In the simplest case, all white voxels belong to the segment (contour) while all black voxels belong to the background.

In order to convert contours into binary images, in DICOM, for example, where a segment is stored as a stack of closed 2D contours, one 2D contour for each slice of the image the contours are meant to annotate, for each voxel in the associated 3D image, it is determined whether the voxel is inside or outside the contour, and a pixel value is assigned accordingly. By analyzing the pixel values of the original images containing the contours and assigning values to the pixels in each image, a plurality of binary images are obtained, in which all pixels (voxels) with a value above the threshold (i.e., value "1") are considered to be within the structure (contour), and all pixels (voxels) with a value below the threshold (i.e., value "0") are considered to be outside of the structure (contour). The computer processing device may analyze the image data and assign a "1" or a "0" value or their equivalents on the fly. The contours within each image are next extracted using any applicable contour extraction processes. Each contour within an image is then saved as a binary image in a storage device associated with the system controller 60 and/or the computer processing device 70, or the external storage device, for further processing.

The binary contour images are next combined using Boolean operations and pixel counting. Boolean operations include a set of logical rules by which binary images can be combined. The four basic Boolean operations are AND, OR, Ex-OR (Exclusive OR) and NOT. Boolean operations can also be combined for more complex image combinations. The operations are performed pixel-by-pixel.

For example, given two binary images A and B, the Boolean combination (A AND B) generates a single image C as a result. The image C will contain only the pixels that have a value "1" in both the A and B images. A Boolean combination (A OR B) generates a single image C as a result, where image C will contain the pixels which have a value "1" in either the A or the B image. A Boolean combination (A Ex-OR B) also generates a single image C as a result, containing the pixels which have a value "1" in either image A or B, but not if the pixels have a value "1" in both images A and B. A Boolean combination (A NOT B) requires only a single image A or B, and the result is an image C where the pixels are reversed, namely, all pixels that had a value "1" in the original image will have a value "0" in the generated image, and the pixels that had a value "0" in the original image will have a value "1" in the generated image. A Boolean combination ((NOT A) AND B) will produce an image C containing pixels that lie within B but outside A. A Boolean combination (NOT (A AND B)) generates an image C containing pixels that do not have a value "1" in both A and B. In a Boolean operation (A-B), the resulting binary image C is an image that contains the volume of the structure of A with the intersecting volume of structure of B removed.

Using Boolean logical rules, any number of binary contour images can be combined (two at the time), and the resulting image analyzed in order to determine whether a heuristic rule has been complied with or has failed (i.e., rule was violated).

For example, if the heuristic rule is that the structure must not overlap with another structure (i.e., one contour must not overlap another contour), the following steps are taken to check whether this rule has been complied with:

1. The computer processing device 70 fetches two binary contour images A and B from the storage device to be analyzed;

2. The binary contour images A and B are combined using a Boolean combination which computes the intersection between the two contours (i.e., Boolean operation (A AND B)). The resulting binary image C is an image that contains the pixels that are assigned a value "1" in both images A and B. This image C will thus include the pixels that are common to both A and B, and thus include the pixels where the two contours intersect. This image C is thus an image of the intersection of the two contours;

3. The pixels (voxels) in the image C, namely, the pixels/voxels in the overlapping region are then counted. The counting can be done using any applicable counting methods. One way of counting the pixels/voxels is by performing a series of one directional passes across the rows and columns of image C to search for the pixels/voxels having a value "1" and storing a count for each of these pixels/voxels;

4. If the number of counted pixels (voxels) is more than zero, a determination is made that an overlap exists;

5. The volume of overlapping region is computed by computing the number of voxels times the voxel size;

6. In order to not report insignificant overlaps (i.e., if the overlap is so small that it is insignificant), the volume of overlapping region is compared with a predetermined threshold volume;

7. If the volume of overlapping threshold region is above the threshold volume, a determination is made that there is a significant overlap between the structures of image A and image B. Since the heuristic rule required that there be no overlap between the structures, a determination is made that the heuristic rule has been violated;

8. A user is alerted that a quality check has failed.

In addition, or alternatively, if the heuristic rule is that the CTV structure is completely covered by a PTV structure (i.e., the PTV contour must completely cover the CTV contour), the following steps are taken to check whether this rule has been complied with:

1. The computer processing device fetches two binary contour images A and B to be analyzed;

2. The binary contour images A and B are combined using Boolean combination which computes the subtraction between the two contours (i.e., Boolean operation (A-B). The resulting binary image C is an image that contains the volume of one structure A with the intersecting volume of structure B removed, and thus it contains the pixels of structure A that is not covered by the structure of B;

3. The pixels (voxels) in the resulting image C are counted. The counting can be done using any applicable counting methods. One way of counting the pixels is by performing a series of one directional passes across the rows and columns of image C to search for the pixels/voxels having a value "1" and storing a count for each of these pixels/voxels;

4. If the number of counted pixels (voxels) is more than zero, a determination is made that the structure of image B is not completely overlapping the structure of image A;

5. The volume of not-overlapping region is computed by computing the number of voxels in the not-overlapping region times the voxel size;

6. In order to not report insignificant no-overlaps (i.e., if the non-overlapped region is so small that it is insignificant), the volume of non-overlapping region is compared with a predetermined threshold volume of non-overlapping region;

7. If the volume of non-overlapping threshold region is above the threshold volume of non-overlapping region, a determination is made that the structure of B is not completely overlapped by the structure of A, and thus the heuristic rule has been violated;

8. A user is alerted that a quality check has failed.

The same functionality (i.e., determining subtraction (A-B) and then counting voxels) may also be used to check the rules "CTV must cover GTV" and "a structure must be inside the contour of the body."

For the heuristic rule "the structure does not contain any empty slices," for each image slice (A, B, etc.) the number of voxels that are assigned a value "1" are counted. If the number of counted pixels (voxels) is above a threshold pixel/voxel number, a determination is made that the image slice is not empty. If the counted pixel/voxel number is less than the predetermined threshold number, a determination is made that the slice is empty, and thus the heuristic rule has been violated.

For the heuristic rule "the length of the shape must be in a predefined typical range," a scan-line approach may be used to pass over the image, identify the voxels that are over a threshold, determine the largest distance between voxel pairs among such voxels, and compare the distance to a threshold length. If the obtained distance is greater or smaller than the threshold length, it is determined that the length of the shape is not within a predefined range.

For the heuristic rule "the volume of the shape must be in a predefined typical range," the voxels of the shape are counted, the voxel count is multiplied by the voxel size, and the result is compared with a threshold volume range. If the volume calculated is outside the predetermined threshold volume range, it is determined that the volume of the shape is not within a predefined range.

For the heuristic rule "the left and right lung structures must not be switched by mistake", the left and right lungs are two separate structures. For each, the center of gravity can be computed. Thereafter, by comparing the position of the centers of gravity of the right and left lungs, it is determined whether they are switched.

In operation, the plurality of binary contour images obtained from the generated image slices (CT, MRI, etc. image slices, for example) are automatically evaluated using a heuristic evaluation method by which two or more images are combined based on one or more heuristic rules using one or more Boolean operations, and the pixels and/or voxels in the resulting image are counted. The number of pixels/voxels in the resulting image determines whether one or more of the heuristic rules have been violated.

In embodiments, a check failure signal can be sent after at least one heuristic rule has been violated. In other embodiments, a check failure signal can be sent after two or more heuristic rules have been violated. In alternative embodiments, one or more heuristic rules are implemented for each quality check.

Although the embodiments have been described using binary images, the heuristic check can also be applied on contours that have not been converted into binary images.

In addition to, or alternatively, the heuristic rules can be checked by performing a 3D connectivity labeling technique. The 3D labeling technique identifies disconnected parts of a segment (contour) by performing a 3D connectivity labeling process which labels all connected components of a structure. When 3D labeling is applied, the quality check fails if more than one component is found for structures that should include only one component.

3D connectivity labeling can also be applied if there is one segment that includes multiple components, such as the lung, which consists of the left and right lung. In such a case, 3D labeling will return the number 2 (for two labels) and will label one lung with value 1 and the other with value 2.

Figure 7:
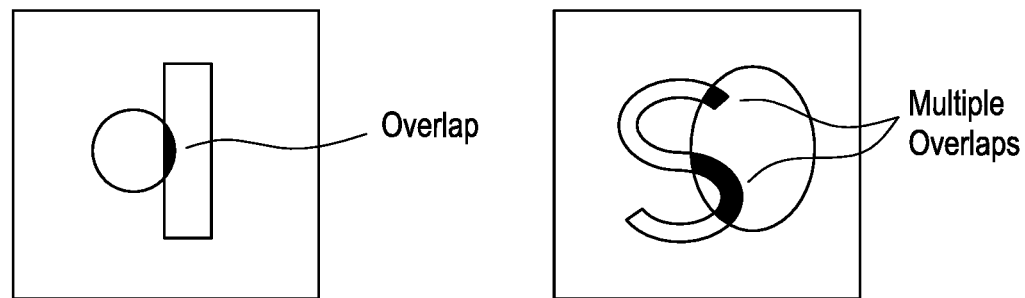
FIG. 7 illustrates examples of segmentations with single and multiple overlaps.

3D labeling can also use a scan-line approach to pass over an image two times, propagating the labels of the segments that have already been encountered. When a new segment is encountered, a new label is added. When labels meet, it means that they actually belong to the same segment, and a method is called to merge the two labels into one label (e.g., by changing both labels to a common new label or by changing both labels into one of the two labels). The same labeling technique may be used to identify if a heuristic rule has been violated in several places and/or to determine in how many spots a quality check fails. For example, when an overlap is detected between two structures (segments), a 3D connectivity labeling may be performed to identify if there are several individual/disconnected overlaps between two structures (e.g., as illustrated in FIG. 7), and the overlaps can be presented to the user individually.

In operation, the plurality of binary contour images obtained from the generated image slices (CT, MRI, etc. image slices, for example) are automatically evaluated using a heuristic evaluation method which is based on performing a 3D connectivity labeling process.

In some embodiments, depending on computational complexity, some or all quality checks are executed on-the-fly as a user edits the contours.

In some embodiments, an alert signal/message can be displayed on a display mechanism of the computer processing device 70 to alert the user of failed quality check. The user may further expand the alert message to see additional details about why and where the quality checks failed. Options to focus the view on the place where the quality checks failed (e.g., showing the location where two structures overlap) and/or providing options to correct the error (e.g., interpolating missing slices, etc.) can also be included.

In some embodiments, the evaluation method is performed in real time, and thus the contours can be evaluated in real time. In addition, or alternatively, in some embodiments, a contouring report may be generated. The contouring report may provide an overview of the current state of contouring, including statistics about the patient, planning images, and results of the quality checks. Upon review of the report, a user may immediately respond to a failure of one or more quality checks, either by redoing the contouring, for example, in order to improve the efficiency and safety of the structure review process by highlighting any potential issues.

Statistical Shape Models Evaluation Method

Statistical shape model evaluation methods are quality checks that perform statistical tests based on previous reliable segmentations of the same organ. Using previous segmentations of sufficient quality and quantity, a "statistical shape model" is built. This model is a probability distribution of shape variations found in the example segmentations. A statistical test tailored to these models may then be performed to check if the shape of a given structure, such as an organ for example, lies within the normal range known for this type of structure/organ.

Alternatively, or in addition to the heuristic evaluation method, the contours can be further automatically evaluated using a statistical shape model evaluation method. This can be done by implementing a statistical shape model evaluation method by the computer processing device 70. This evaluation method defines a probability distribution to model the normal variation of the shape of an organ. In one embodiment, this distribution is a multivariate normal distribution $\mathcal{N}$ ($\mu$, $\Sigma$) defined over the space $\mathbb{R}p$ of deformations of a predefined reference organ $x_0$. The parameters of the multivariate normal distribution $\mathcal{N}$ ($\mu$, $\Sigma$) are the mean $\mu$ and the covariance matrix $\Sigma$ that are estimated from a set of examples $x_1, \ldots, x_0$ as:

$$\mu = \frac{1}{n}\sum_{i=1}^{n} x_i$$

$$\sum = \frac{1}{n}\sum_{i=1}^{n} (x_i - \mu)(x_i - \mu)^T$$

Figure 9:
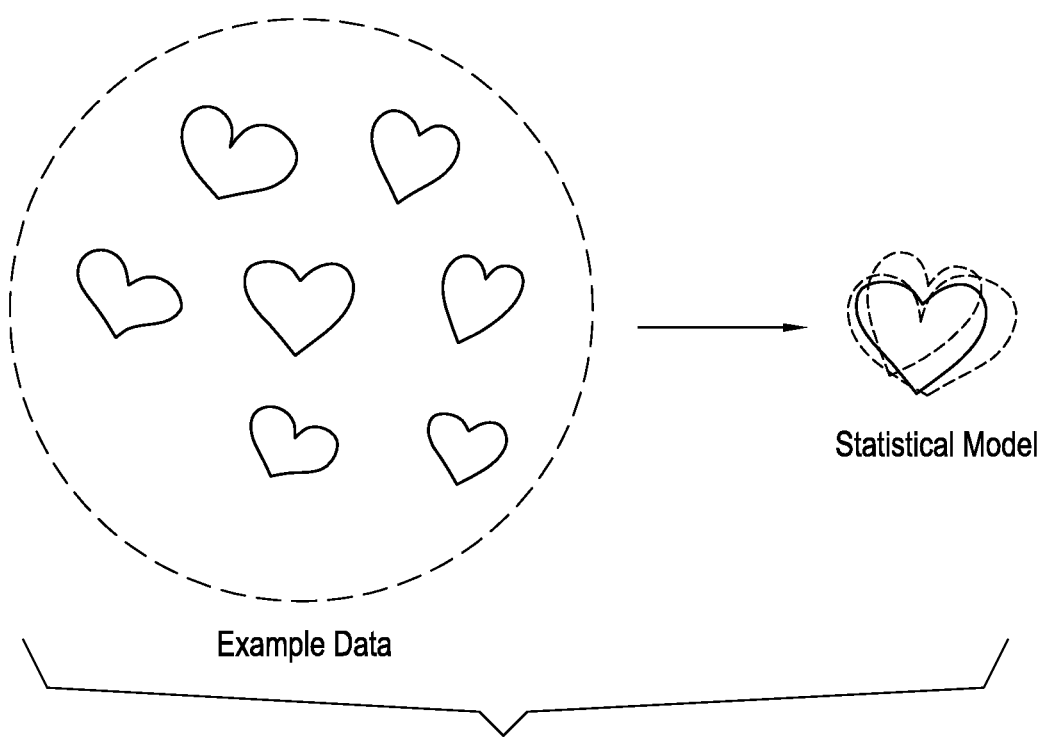
FIG. 9 illustrates a shape model that uses example data to represent the shape variation of an organ, according to embodiments of the present invention.
Figure 10:
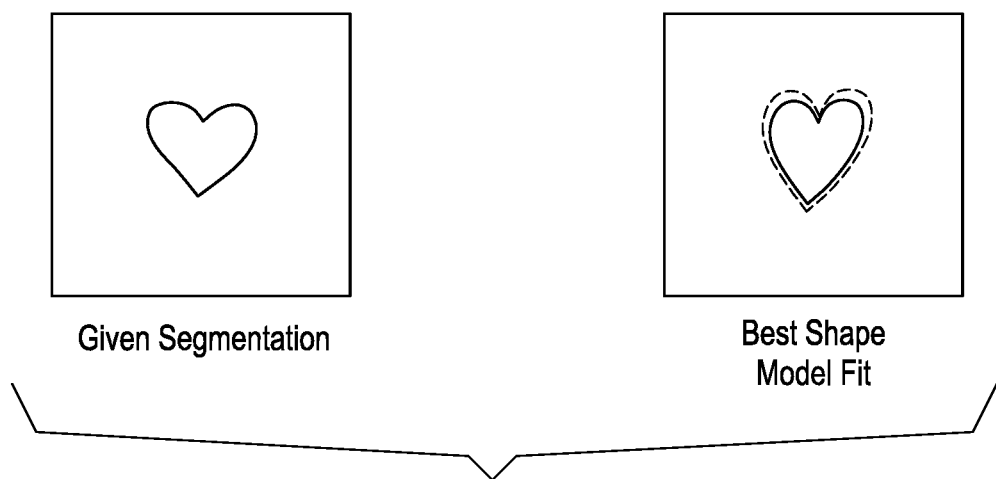
FIG. 10 illustrates an example of using shape model fitting to assess a given segmentation, according to embodiments of the present invention.

FIG. 9 illustrates a shape model that uses example data to represent the shape variation of an organ. Depending on the type of model used, the space of deformations may be defined over only the shape $x_0$ or over its surrounding space $\mathbb{R}p$. In one embodiment, in order to model the example shapes as deformations of a reference shape, the example shapes need to be brought into correspondence by "non-rigid registration" (due to biological differences and/or due to image acquisition, localized stretching of images is needed in order to achieve correspondence between structures in two images). The non-rigid registration algorithm computes the example deformations $x_1, \ldots, x_n$ from which the shape model parameters can be estimated as shown above.

A principal component analysis (PCA) can be performed in order to efficiently store and handle a shape model. PCA is a statistical algorithm that implements an orthogonal transformation to convert a set of observations of possibly correlated variables into a set of values of linearly uncorrelated variables called principal components. PCA essentially provides a diagonalization of the covariance matrix $\Sigma$. The term "RCA models" commonly refers to statistical shape models. In order to construct a statistical shape model, a mean shape and a number of modes of variation from a collection of training samples (e.g., previous segmentations of an organ) can be extracted. Some examples of statistical shape models as PCA models that can be used in the disclosed embodiments are disclosed in "Statistical shape models for 3D medical image segmentation: a review," T Heimann et al., in Medical image analysis, 2009, which is incorporated herein by reference in its entirety.

In order to check if a given new segmentation of an organ fits the shape model built from previous segmentations of that organ, it is determined how probable the new segmentation is under the multivariate normal distribution $\mathcal{N}$ ($\mu$, $\Sigma$) built from previous segmentations. In order to do so, in one embodiment the probability density distribution of the multivariate normal distribution $\mathcal{N}(\mu, \Sigma)$ is directly evaluated. In another embodiment, the statistical shape model is used to compute the probability of observing a segmentation that is as probable or less probable than a given segmentation. This can be computed from the statistical shape model with a statistical test and quantified with a probability value (p-value) between 0 and 1. As such, a threshold value (e.g., 5%, for example) can be chosen below which a segmentation is deemed too improbable to accept. Alternatively, the p-value can be displayed to the user to judge the probability they are willing to accept.

An example of a statistical test is disclosed in "Process monitoring based on probabilistic PCA (PPCA)," Dongsoon Kim et al., Chemometrics and Intelligent Laboratory Systems, 2003 (hereinafter "Kim"), incorporated herein by reference in its entirety, where the statistical test is based on PPCA and the objective of the statistical test is detecting abnormal events of a process with respect to a process model. Such a statistical test based on PPCA for detecting abnormal shapes with respect to a shape model, can be applied in embodiments of the disclosed evaluation method.

PPCA is an extension to the PCA models described above, and, in addition to the normal shape variations described by the PCA model, models the admissible deviation from the model by white-type noise with negligible amplitude or variance, which may result in abnormal means of variables, abnormal variance of variables, and/or abnormal correlations among variables. The abnormality may be judged by statistical testing for the elements of a given segmentation. PPCA is based on a probabilistic generative model where the measurement variable x is assumed to be the output of the linear combinations of mutually uncorrelated input variable z plus additive noise e, and where some probability densities are specified for the variables in the model. PPCA aims to find the most probable parameter set:

$$\Theta = \{A, \lambda\}$$

in the model structure:

$$x = A \cdot z + e$$

where A is the loading matrix and $\lambda$ is the covariance matrix of e which is Gaussian with zero mean. In one embodiment, the parameter set can be estimated by the "expectation and maximization" algorithm, which is an iterative likelihood maximization algorithm.

A given segmentation needs to be available in a suitable mathematical representation in order to assess it with a statistical shape model test. That is, a given segmentation needs to be represented as a deformation of the model's reference organ. In order to do that, one embodiment implements functionality similar to the building phase of the model to achieve such representation of the given segmentation with non-rigid registration. This registration implements an optimization algorithm that finds a deformation of the reference that best matches the given segmentation. In order to make the optimization more efficient and robust, "model fitting" is implemented and the search space of the optimization is restricted to the span of the statistical shape model. The result can then be assessed with a statistical test (e.g., with the statistical test of Kim, for example).

In an exemplary embodiment, "model fitting" includes the process of finding the shape model parameters which best explain the given data. It is an optimization procedure which minimizes the distance between the current model instance and the given data. Model fitting is applicable to the present embodiments since the PPCA model is a generative model, which means it can generate instances of the model, which can be directly compared to the input data. In the aforementioned model structure, this means finding z so that A·z is as close to x as possible. Because the model is built from a finite set of example data sets, the term A·z may not perfectly represent the infinite variability of every possible input data, no matter if it is the correct type of organ or not. In the PPCA model, this is modeled by the noise term e. So even if the optimization has found a set of parameter z so that A·z is very close to x, a residual may remain. Accordingly, the statistical test may check two sets of values: a within-model probability (i.e., the probability of the best fit within the span of the model) and a residual between the model fit and the given segmentation. That is, one part of the test is to determine if this residual is small enough to be explained by the noise variable e (i.e., the probability of the residual), and the other term that needs to be tested is the set of model parameters z.

For example, even if A·z is very close to x, the parameters computed by the optimization to achieve this close fit may be very extreme. So the second test is to determine if these variables are in accordance with the PPCA model (i.e., the within-model probability). The matrix A in the PPCA model is configured so that the variables z are N (0, I) distributed, which means each variable has a 1D normal distribution with no correlation between the variables. Similarly, the noise variable e models only uncorrelated Gaussian noise. Due to this uncorrelated model, each variable's contribution to the statistical test can be assessed individually. These two checks (i.e., related to within model probability and residual) may be aggregated or may be considered individually.

The spatial relation of organs can be further modelled as disclosed in "Automated contouring error detection based on supervised geometric attribute distribution models for radiation therapy: A general strategy," Hsin-Chen Chen, et al., Medical Physics, 2015 (hereinafter "Chen"), which is incorporated by reference herein in its entirety. This modeling models the relative spatial relation of several organs in a "geometric attribute distribution" (GAD), which is a model of centroid, volume and shapes of a set of organs. The shape characteristics of the individual organs are modeled by statistical shape models that are based on linear combinations of signed distance maps. Accordingly, when such further modeling is applied, a further statistical modeling of the relative position of the organs at risk with respect to each other is performed. Alternatively, the relative position of the organs at risk with respect to each other may be checked with heuristic rules.

In operation, in addition to, or as an alternative to the heuristic evaluation method, a segmentation (i.e., contour) can be further evaluated using a statistical shape model evaluation method. In order to do that, first the segmentation is converted to a mathematical representation, namely, the segmentation is represented as a deformation of the model's reference organ. Then the deformation is assessed using a statistical test, such as a probabilistic PCA test, to determine if a given structure (contour) is in accordance with the statistical shape model. If it is, then it is determined that the shape of the organ lies within the normal range known for this type of organ. If it is not, then it is determined that the shape of the given organ lies outside of the normal range known for this type of organ, and therefore the contour contains errors. In such an instance, a user may be alerted that the quality check has failed. The user may further expand the alert message to see additional details about why and where the quality checks failed. Embodiments also provide options to focus the view on the place where the quality checks failed (e.g., showing the location where the difference between the segmentation and the shape model is largest) and/or provides options to correct the error (e.g., interpolating missing slices).

Depending on computational complexity, some quality checks (heuristic and/or statistical) are executed on-the-fly as a user edits the contours. Further, the statistical and/or heuristic quality checks can be provided in real time. A contouring report may also be displayed to provide an overview of the current state of contouring, including statistics about the patient, planning images, and results of the quality checks.

Figure 4:
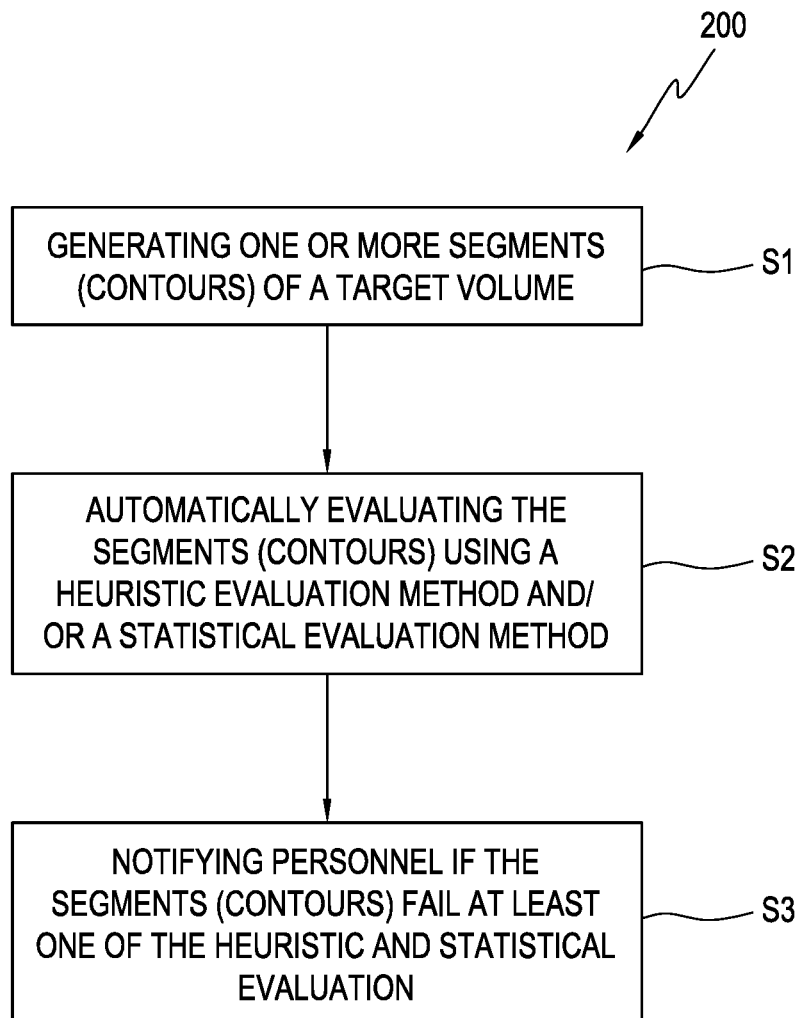
FIG. 4 illustrates a segment error detection process according to one or more embodiments of the disclosed subject matter.

An automatic real time segment (contour) error evaluation method 200 is illustrated in FIG. 4. In step S1, one or more segments (contours) are generated. This can be done using any of the available manual, semiautomatic and automatic contouring tools and methods on each of the generated CT slices. In S2, the segments (contours) are automatically evaluated by a computer processing device using a heuristic evaluation method and/or a statistical evaluation method. The heuristic evaluation method includes checking whether one or more of a set of heuristic rules implemented using Boolean operators and pixel/voxel counting and/or a 3D connectivity labeling process have been violated.

The statistical evaluation method includes using a statistical shape model evaluation method to assess, using a statistical test, such as a probabilistic PCA test, for example, if a given shape of an organ lies within the normal range known for this type of organ. In S3, an authorized personnel is notified that at least one of the heuristic rules and/or the statistical rule is violated, which is an indication of an error in either the segment (contour) and/or an error in the shape of the contour (i.e., organ).

FIGS. 11 and 12 illustrate exemplary quality checks performed on different input segmentations (contours) using a statistical evaluation method. The segmentation (contour) B shown in FIG. 11A is that of a brachial plexus including a right side segmentation portion B2 and a left side segmentation portion B1 (i.e., their surface representations). The quality check performed on segmentation B includes checking if the segmentation B fits a corresponding shape model's (i.e., shape model M shown in FIG. 11B) probability distribution $\mathcal{N}(\mu, \Sigma)$. The shape model M shown in FIG. 11B represents the model mean (e.g., the mean of a set of previous segmentations of the same organ). FIG. 11C shows the result of the model fitting of segmentation B in accordance with the shape model distribution defined by $\mathcal{N}(\mu, \Sigma)$. The best fit is the model instance according to the computed parameters z. It is clearly shown in FIG. 11C that the model M can be fitted to the input shape (i.e., segmentation B) quite well and the residual is small. But the within-model probability of the model parameters z is still low because the parts of the shape that extend to the left (P1) and the right (P2) are too small. Because the quality check has detected that the left and right protrusions P1, P2 of the shape are too small, the segmentation (contour) B fails quality check. If the protrusions P1, P2 would have fit within a previously determined acceptable size range, the quality check of segmentation B would have passed.

The input segmentation (contour) C shown in FIG. 12A is also that of a brachial plexus. In this case, however, there is only a left side segmentation portion C1, with the right side segmentation portion C2 missing. The quality check performed on segmentation C also includes checking if the segmentation C fits a corresponding shape model's (i.e., shape model M shown in FIG. 12B) probability distribution $\mathcal{N}(\mu, \Sigma)$. The shape model M shown in FIG. 12B represents the model mean (e.g., the mean of a set of previous segmentations of the same organ). FIG. 12C shows the result of the model fitting of segmentation C in accordance with the shape model distribution defined by $\mathcal{N}(\mu, \Sigma)$. It is clearly shown in FIG. 12C that because the input shape (i.e., segmentation C) is missing half of the brachial plexus (i.e., missing segmentation C2), the fitting is not really possible, resulting in both a high residual and a very improbable model parameters z. Therefore, the segmentation (contour) C fails quality check.

In embodiments, the heuristic quality checks are configured to identify common mistakes, such as missed slices and misplaced contours, with efficient and clear heuristic rules. In embodiments, the use of accurate shape models that are based on point correspondence and registration, are implemented to statistically evaluate the shapes of structures under evaluation.

Some or all of the quality checks of the present embodiments can be used in other applications in which manual or automatic segmentation of images (2D, 3D, and/or 4D) is performed and the segmentations need to be evaluated and controlled. Examples of such applications are medical image segmentation for operation planning, segmentation for quantitative measurements, etc.

Some or all of the quality checks of the present embodiments can also be used to evaluate the plurality of segmentations used to generate a segmentation model, and therefore perform an overall quality check of the segmentation model prior to be used to evaluate a contour. For example, for a segmentation model M generated based on previously obtained plurality of segmentations (contours), a heuristic evaluation can be applied to verify that the segmentations pass the applied heuristic rules. If the segmentations, or if a predefined percentage of the segmentations pass the heuristic evaluation, it can be concluded that the segmentation model M, which may be used for the statistical evaluation of a contour at a later time, is indeed correct.

Embodiments are also applicable even when segmentation of the objects is trivial (e.g., in photographs of produced or manufactured goods) where the quality checks of the embodiments can be employed to control if the given object adheres to predefined standards. One such application is agricultural or industrial quality control.

Embodiments are further applicable in data mining when all structures of a certain kind need to be extracted from a database for further analysis (e.g., all segmentations of a given organ). Examples of such applications are retrospective clinical trials and knowledge based radiotherapy planning. In databases, structures are usually assigned a name or a label. Since these names are assigned and entered by a user, they may be ambiguous and/or incorrect. Accordingly, by running the quality checks on all structures, or, more efficiently, those that have been preselected based on their names, embodiments can assure that only correct structures of the desired kind are selected.

Alternative embodiments may implement various other statistical shape models such as, for example, Active Shape Models, Active Appearance Models, Morphable Models, Statistical Deformation Models, and Distance Map-based shape models. In some alternative embodiments, the statistical shape model-based checks can be based on any of these statistical methods aiming at representing the variety of shape and/or appearance of an organ.

In some alternative embodiments, the shape model checks and/or the heuristic rules may be implemented with other representations of the structures, such as, for example, surface meshes, volumetric meshes, implicit functions, images, or contour lines.

In further embodiments, automatic quality checks can be performed by implementing the quality checks in radiotherapy contouring software. In other embodiments, quality checks are provided in a quality report within the contouring software. Other embodiment, provide quality checks with live indication in a user interface of the contouring software. One embodiment identifies, displays, and navigates to individual regions where quality checks have failed. One embodiment provides semantic knowledge about organs in radiotherapy contouring software to allow for organ-specific rule application. One embodiment uses statistical shape models for quality control (e.g., the statistical shape model of Kim, for example). One embodiment uses a statistical shape model in radiotherapy (e.g., the statistical shape model of Kim, for example). One embodiment uses a statistical test for shape modeling (e.g., the statistical test of Kim, for example). One embodiment uses a statistical test in radiotherapy (e.g., the statistical test of Kim, for example).

It will be appreciated that the processes, systems, and sections described above can be implemented in hardware, hardware programmed by software, software instruction stored on a non-transitory computer readable medium or a combination of the above. For example, a method for can be implemented using a processor configured to execute a sequence of programmed instructions stored on a non-transitory computer readable medium. The processor can include, but not be limited to, a personal computer or workstation or other such computing system that includes a processor, microprocessor, microcontroller device, or is comprised of control logic including integrated circuits such as, for example, an Application Specific Integrated Circuit (ASIC).

The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms.

Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, an automatic segmentation and contour evaluation method implemented by a computer processing device. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A method for detecting a segmentation error in a segment representing a delineation of an anatomical structure of a subject on an image, comprising:
   selecting an appropriate segment evaluation method from a plurality of segment evaluation methods available to be applied on the segment, the plurality of evaluation methods including a heuristic evaluation method and a statistical evaluation method; and
   evaluating the segment using the selected evaluation method,
   wherein the heuristic evaluation method includes evaluating whether one or more of a set of heuristic rules are violated, and the statistical evaluation method includes evaluating whether a shape of the segment is within a predetermined range of known shapes for the segment; and providing a signal indicating that an error in the segmentation is present based on a result of the evaluating.

2. The method of claim 1, wherein the determining whether one or more of the heuristic rules are violated includes using Boolean operators and pixel/voxel counting.

3. The method of claim 2, wherein the determining whether one or more of the heuristic rules are violated using Boolean operators and pixel/voxel counting comprises:
generating binary images for the segment;
combining the binary images using at least one of a plurality of Boolean operators to obtain a resulting binary image; and
counting pixels/voxels in the resulting binary image,
wherein a heuristic rule is violated if the number of pixels/voxels is not within a predetermined range.

4. The method of claim 1, wherein the determining whether one or more of the heuristic rules are violated includes using a 3D connectivity labeling process.

5. The method of claim 4, wherein using the 3D connectivity labeling process includes identifying disconnections in the segment by:
determining how many segment components does the segment have; and
comparing the number of the segment components with a previously determined number representing the number of connected components delineating the anatomical structure,
wherein a heuristic rule is violated if the number of segment components is different from the previously determined number of connected components.

6. The method of claim 1, wherein the evaluating whether the shape of the segment is within a predetermined range of known shapes for the segment includes:
generating a statistical shape model for the segment; and
determining whether the shape of the segment is within a predetermined range of known shapes for the segment,
wherein a segmentation error is present if the shape of the segment is not within the predetermined range.

7. The method of claim 6, further comprising:
generating the shape model based on a probabilistic distribution of shape variations found in the range of known shapes for the segment; and
performing a statistical test to check if the shape of the segment is within the predetermined range.

8. The method of claim 7, wherein the probabilistic distribution includes a multivariate normal distribution $\mathcal{N}(\mu,\Sigma)$, and the performing of the statistical check comprises evaluating how well the segment shape fits within the multivariate normal distribution using a probabilistic principal component analysis (PPCA),
wherein if the shape of the segment does not fit within the multivariate normal distribution within a predetermined value, it is determined that a segmentation error is present.

9. The method of claim 1, wherein the evaluating is automatically performed after generating the segment on the image.

10. The method of claim 9, wherein the generating of the segment on the image is by one of an automatic, manual, or a combination of automatic and manual segmentation.

11. The method of claim 10, wherein the generating of the segment and the evaluating of the segment are performed by same device.

12. The method of claim 10, wherein the generating of the segment and the evaluating of the segment are performed by different devices operably connected to each other.

13. The method of claim 1, further comprising providing information regarding the nature and location of the detected segmentation error.

14. A system for detecting a segmentation error in a segment representing a delineation of an anatomical structure of a subject on an image, the system being configured to:
select an appropriate segment evaluation method from a plurality of segment evaluation methods available to be applied on the segment, the plurality of evaluation methods including a heuristic evaluation method and a statistical evaluation method;
evaluate the segment using the selected evaluation method, the heuristic evaluation method including evaluating whether one or more of a set of heuristic rules are violated, and the statistical evaluation method including evaluating whether a shape of the segment is within a predetermined range of known shapes for the segment; and
provide a signal that an error in the segmentation is present based on a result of the evaluating.

15. The system of claim 14, comprising a database including the set of heuristic rules.

16. The system of claim 14, wherein the system is configured to determine whether one or more of the heuristic rules are violated using Boolean operators and pixel/voxel counting.

17. The system of claim 16, wherein the system is further configured to:
generate binary images for the segment;
combine the binary images using at least one of a plurality of Boolean operators to obtain a resulting binary image;
count pixels/voxels in the resulting binary image; and
signal that a heuristic rule is violated when the number of pixels/voxels is not within a predetermined range.

18. The system of claim 14, wherein the system is further configured to determine whether one or more of the heuristic rules are violated using a 3D connectivity labeling process.

19. The system of claim 18, wherein the system is further configured to:
identify disconnections in the segment by determining how many segment components does the segment have; and
compare the number of the segment components with a previously determined number representing the number of connected components delineating the anatomical structure,
wherein a heuristic rule is violated if the number of segment components is different from the previously determined number of connected components.

20. The system of claim 14, wherein the system is further configured to:
evaluate whether the shape of the segment is within a predetermined range of known shapes for the segment by generating a statistical shape model for the segment; and
determine whether the shape of the segment is within a predetermined range of known shapes for the segment,
wherein a segmentation error is present if the shape of the segment is not within the predetermined range.

21. The system of claim 20, the system being further configured to generate the shape model based on a probabilistic distribution of shape variations found in the range of known shapes for the segment and perform a statistical test to check if the shape of the segment is within the predetermined range.

22. The system of claim 14, wherein the system is configured to automatically perform the segment evaluation after the segment is generated on the image.

23. The system of claim 22, further comprising a device for generating the segment on the image by one of an automatic, manual, or a combination of automatic and manual segmentation.

\* \* \* \* \*